United States Patent [19]
Guimbretiere

[11] 3,985,096
[45] Oct. 12, 1976

[54] APPARATUS FOR COLORING SLIDES

[75] Inventor: Jean Gerard Guimbretiere, Nantes, France

[73] Assignee: Association du Centre de Transfusion Sanguine et de Dessiccation du Plasma, Nantes, France

[22] Filed: Feb. 27, 1975

[21] Appl. No.: 553,663

[30] Foreign Application Priority Data
Mar. 6, 1974   France .............................. 74.08242

[52] U.S. Cl. ................................ 118/58; 118/236; 118/324; 8/3; 214/1 BS; 427/2
[51] Int. Cl.² ....................... B05C 1/02; B05C 13/00
[58] Field of Search ............. 118/58, 300, 313, 314, 118/324, 50, 236; 269/21, 22; 8/3; 94.11; 214/1 BS; 427/2; 134/126, 128, 133

[56] References Cited
UNITED STATES PATENTS

| 1,315,740 | 9/1919 | Milmoe ........................... 118/236 X |
| 2,011,098 | 8/1935 | Wettlauper ..................... 118/236 X |
| 2,203,572 | 6/1940 | Johnson .............................. 269/21 |
| 2,380,968 | 8/1945 | Kimmig et al. ........................ 118/58 |
| 2,646,769 | 7/1953 | Lindsay .............................. 118/313 |
| 2,995,482 | 8/1961 | Boyce et al. .......................... 118/58 |
| 3,467,060 | 9/1969 | Klebanow et al. .............. 118/236 X |
| 3,667,896 | 6/1972 | McCormick et al. ...................... 8/3 |
| 3,837,795 | 9/1974 | Becker et al. ............................. 8/3 |
| 3,876,465 | 4/1975 | Prazak ........................... 118/324 X |
| 3,908,835 | 9/1975 | Lubas ............................... 214/1 BS |

FOREIGN PATENTS OR APPLICATIONS 1,166,088   10/1969   United Kingdom ................. 118/236

Primary Examiner—James Kee Chi
Attorney, Agent, or Firm—Laff, Whitesel & Rockman

[57] ABSTRACT

The invention provides for applying a treatment medium such as blood smears to slides. A plurality of suction cups are adapted to be conveyed in an endless path, defining a loading station. Smear slides are pushed upon and attached one by one to the suction cups. At a treatment station, a treatment medium can be applied to a smear on the side of a slide opposite the suction cup.

11 Claims, 5 Drawing Figures

APPARATUS FOR COLORING SLIDES

The present invention concerns apparatus for applying treatment medium to slides such as slides carrying smears, in particular blood smears.

The preparation of blood smears comprises the spreading out of a drop of blood on a glass slide, then the coloring and the fixing of the fine film of blood by means of appropriate reactive liquid treatment mediums. In one well known method, first a few drops of a May Grunwald reagent are poured onto the slide, and then secondly water of equal volume is added, the mixture being spread out on the slide so as to impregnate the fine film of blood in a homogenous manner. Finally and thirdly there is poured onto the slide a quantity of Giemsa reagent diluted sufficiently to cover the smear completely, this reagent requiring to be prepared immediately before use thereof.

At present, in most analysis laboratories, these various operations are generally effected manually. Because of this, they have a certain number of disadvantages. Firstly, the mixture constituted by the water and the May Grunwald reagent has such a surface tension that it spreads out badly and tends to remain in the form of drops. It is necessary therefore to incline the slide to cause the drops to roll over the slide and care must be exercised to avoid the falling of the drops from the slide. In addition, between the various additional operations, well determined times must pass, and it is sometimes difficult to monitor these times when a large number of slides are treated. Finally, as has already been mentioned, the Giemsa reagent must be prepared immediately before use and consequently the manual preparation of the slides is not always perfect and it is especially difficult to obtain homogenous colorings which are desirable for the proper examination of the slides under a microscope.

One object of the present invention is to provide an apparatus which is free from the aforesaid disadvantages.

An automatic coloring apparatus is already known in which the slides are conveyed horizontally on a plate whilst retaining a capillary space between plate and slide for introducing the treatment mediums. However, this apparatus does not permit of using the various reagents such as those quoted above, with the result that the final colorings differ from those to which the operators are accustomed.

There also exist apparatus in which the coloring operations are effected by soaking in the reagents. These apparatus have two drawbacks. In the course of the treatment of one series of slides, there is progressive impoverishing of the coloring baths, which renders the colorings non-uniform. In the course of the soaking, both faces of the slide are colored, which makes cleaning of the non smear carrying side of the slide necessary before examination of the smear under a microscope.

An ancillary object of the invention, in its preferred form, is to provide an apparatus with automatic operation which does not have the above-mentioned drawbacks and which has the advantages of being able to effect all the colorings carried out at the present time manually whatever the reagents used, and of being able to regulate the times of treatment by these reagents, the reagents being added with a concentration independent of the number of slides together and the backs of the slides being protected in the course of the colorings.

According to the invention there is provided apparatus for applying treatment medium to slides, such as slides carrying blood smears, comprising a plurality of suction cups, conveying means supporting said cups and adapted to convey the suction cups in an endless path, means defining a loading station at which smear slides may be attached one by one to the suction cups by being pressed thereto, means defining an unloading station at which the slides may be detached from the suction cups, and means defining at least one treatment medium station at which treatment medium can be applied to a smear on the side of a slide opposite to the side attached to a suction cup when such slide is located in a horizontal section of said endless path and the cup is located under the slide.

Also, according to the invention, there is provided apparatus for applying treatment medium to slides, such as slides carrying blood smears, comprising an endless conveyor carrying suction cups of elastic material to which the backs of the slides adhere in operation of the apparatus, a loading station for pressing each slide to be treated onto a suction cup and an unloading station for detaching the slides from the suction cups, the path of the said conveyor having an upper horizontal reach above which are disposed one or more treatment distributors, and a lower horizontal reach, means defining a drying zone, at said lower reach, an unloading zone and a loading zone these latter zones being respectively opposite the unloading station and the loading station, and said conveyor having connecting curve reaches between the said horizontal reaches, the arrangement being that the planes of the slides are practically horizontal when they travel in the horizontal reaches of the conveyor.

According to a preferred feature, the movement of the endless conveyor is a step by step movement, appropriate drive means being provided, each step being equal to the distance between adjacent suction cups, which are equally pitched.

According to another preferred feature, the said loading station comprises a spring loader for containing the slides to be treated, the said means for application of the slides on the suction cups serving to push the loader towards the suction cup which is located opposite the slide above the loader, at each stop between two steps of the conveyor, so that the slide above the loader distorts the suction cup by a predetermined amount and for releasing the slide of the loader when this predetermined amount of distortion is reached.

According to another preferred feature, the said unloading station comprises a travelling band located below the lower horizontal reach of the said conveyor, and a fixed stop located in the path of travel of the suction cup, so as to deform the latter and cause the entry of air in the cavity of the suction cup, which releases the slide which it carries, which slide falls onto the travelling band which causes it to slip into a slide container.

According to another preferred feature of the invention, the distributors respectively have outlets located to be in register with suction cups when the conveyor dwells between steps, said distributors being adapted to operate at each stop of the conveyor in order to pour a predetermined but adjustable quantity of medium per distributor.

According to another preferred feature, the said outlets each have an outlet pipe and a directing device of the said outlet pipe provided with a counterweight, the said counterweight turning the directing device so as to direct the discharge of the said outlet pipe outside the suction cup when the latter does not carry any slide and being raised by the slide to direct vertically the said jet towards the slide when the suction cup carries a slide.

According to another preferred feature, the apparatus also comprises rinsing water distributors which are located to be opposite respective suction cups upon stopping of the conveyor in dwell positions, said rinsing water distributors being adapted to operate either continuously or at a certain adjustable time after each stopping of the conveyor.

According to another preferred feature, the said conveyor comprises two link chains driven by two toothed pinions the two chains being parallel and coupled by transverse rods extending, the suction cups being carried respectively by plates, each of said plates having at the front of their lower faces a groove in which the transverse rods respectively are engaged.

According to another preferred feature, the said conveyor has associated with the upper reach and partially with the lower reach, horizontal guides which serve to keep the said plates horizontal as well as to provide ramps to cause each plate to tilt, at a predetermined location around transverse rod by which it is guided.

According to another preferred feature, the apparatus includes means for raising or lowering slightly a chain and if necessary lowering or raising the other chain in order to incline in turn the slides carried on the suction cups transversely in respect of their direction of movement.

An embodiment of the invention will now be described, by way of example, with reference to the accompanying drawings, wherein.

Figure 1:
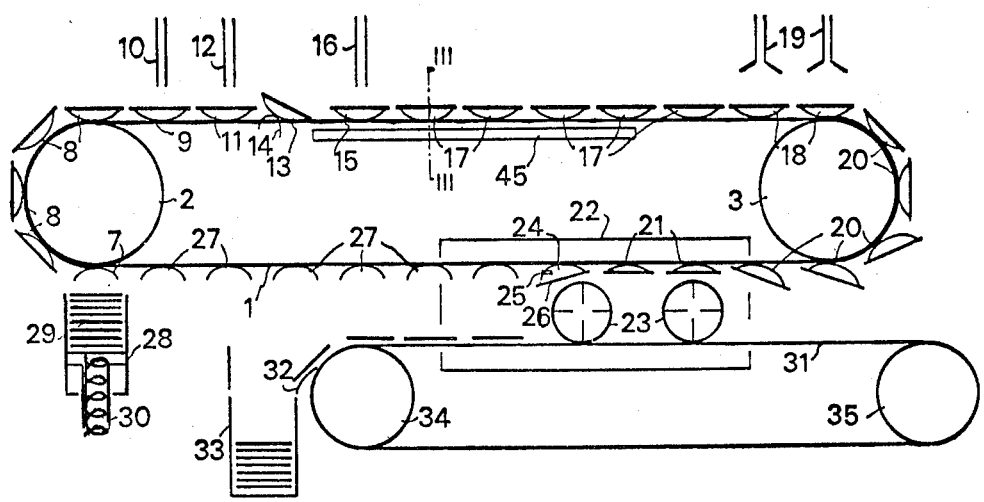
FIG. 1 is a diagrammatic longitudinal sectional elevation showing the whole of the apparatus according to the embodiment of the invention.

The treatment medium application apparatus of FIG. 1 comprises an endless band conveyor 1 trained around two cylinders 2 and 3 one at least of which is driven. The endless band in the embodiment is constituted by two link-chains 4 and 5 (see FIG. 2) connected by rods 6, and the cylinders 2 and 3 have at each of their ends pinions meshing with the links of the chains 4 and 5.

The conveyor 1 transports the suction cups which uniformly are distributed over its whole length. If one considers that the conveyor is in the stopped position in FIG. 1, one can see a suction cup at location 7 ready to receive a slide, a certain number of suction cups at intermediate locations 8 carrying slides respectively towards the treatment zone, a suction cup at treatment location 9 with slide under the May Grunweld reagent distributor 10, assuming that the slides are to be subjected to the preparation indicated herein, a suction cup at location 11 with a slide, under water distributor 12, a suction cup at location 13 inclined above a lump back or ramp 14, a suction cup at location 15 with a slide under the dilated Giemsa reagent distributor 16, a certain number of suction cups at location 17 carrying slides, suction cups at locations 18 with slides under the rinsing water distributors 19, a certain number of suction cups at location 20 carrying slides towards the drying and heating zone, suction cups at locations 21 traversing the drying zone, defined by a tunnel 22 in which one or more fans 23 cause hot air to circulate therethrough, a suction cup at location 24 which is deformed under the action of a fixed stop 25 to allow the slide 26 which it previously carried to fall, and finally a certain number of suction cups at locations 27 without slides.

Below the location 7 there is located a loader 28 containing a batch of slides 29 urged upwards by a spring, so that the first slide of the batch is brought to the same level as the upper part of the loader 28. A motor (not shown) is adapted to raise the stack of slides until the suction cup at location 7 is sufficiently flattened out to hold the first slide firmly.

Under the conveyor 1 is located an endless travelling band 31. This band 31 collects the slides such as 26 which fall at location 24 opposite the stop 25, and band 31 conveys the slides towards a chute 32 which guides these slides towards a conventional container 33. The band 31 is driven by at least one of the two guide rollers 34 and 35, which may also tension band 31.

Figure 2:
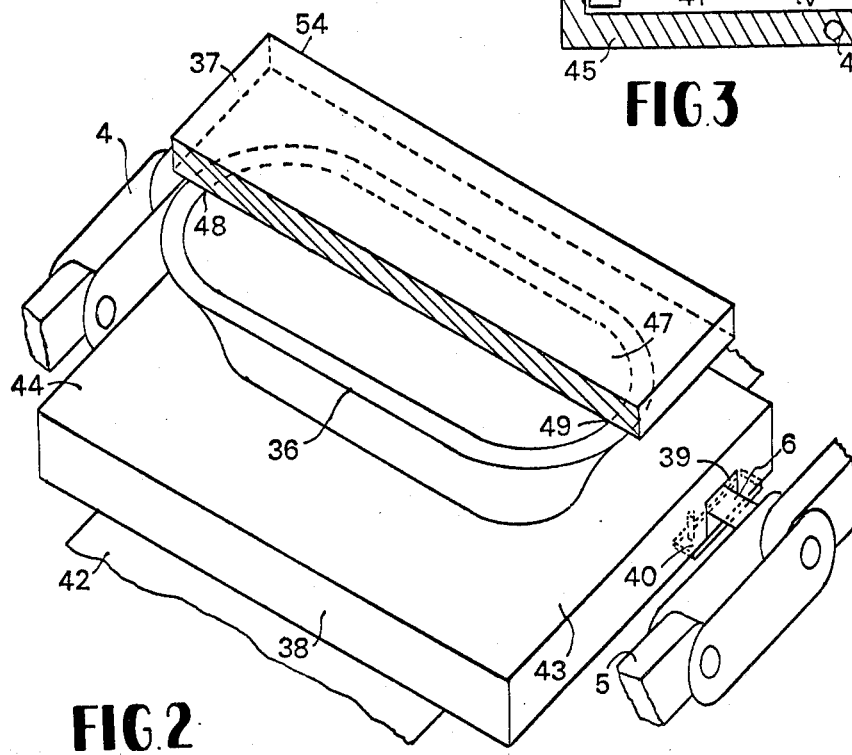
FIG. 2 is a perspective view of a suction cup carrying a slide and a corresponding part of the conveyor used in the apparatus of FIG. 1.

FIG. 2 shows in more detail, how a suction cup 36 supports a slide 37. The bottom of the suction cup 36 is fixed on a rectangular plate 38 which has a groove 39 parallel to its front edge (having regard to the direction in which the plate moves) and hollowed out towards the front of the plate 38. In the groove 39 is loosely located a rod 6 which joins together two axles of links respectively of the chains 4 and 5. The rod 6 is located in the groove 39 by two pivotable plates 40 and 41 or any equivalent means capable of preventing the plate from becoming detached from the rod 6 when the suction cups carried thereby are in any of locations 20, 21, 24 or 27. Between the chains 4 and 5, and the plate 38, there is provided a sheet-metal guide 42 which may present one or more hump-backs or ramps such as 14. It should be noted that the guide 42 is fixed and only exists along the underside of the upper reach of the conveyor 1. As regards the lower reach of conveyor 1 there are provided lateral sheet metal guides at the locations 21 and 24 to keep the plates 38 horizontal, the edges 43 and 44 of plates 38 being supported on these lateral guides (not shown in order to simplify the drawing).

Figure 3:
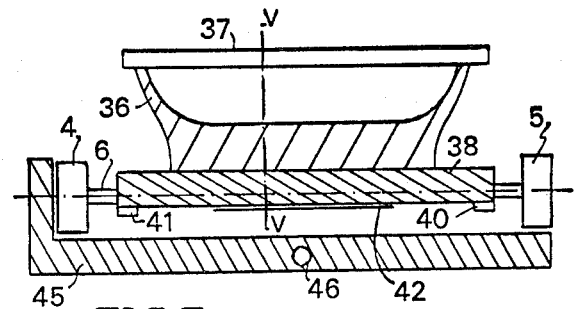
FIG. 3 is a cross-sectional view of the part of the apparatus of FIG. 1, the section being taken on the line III—III of FIG. 1.

The sectional view of FIG. 3 shows in section the relative positions of the slide 37, the suction cup 36, the plate 38 and the chains 4 and 5. It shows furthermore a deflector plate 45 of L-shaped cross-section which can pivot around an axle 46 and take up relatively small inclinations relative to the horizontal. When the plate 45 turns slightly in clockwise direction in FIG. 3, it lifts the chain 4 whilst the chain 5 is allowed to fall under the action of its weight. The consequence is that the upper plane of the slide 37 is likewise inclined. When the plate 45 is tilted in the opposite direction, an inverse inclination of slide 37 is obtained. It is to be mentioned that the plate 45 exists only under the upper reach of the course of the conveyor 1, substantially as FIG. 1 shows.

It should be noted furthermore that the plate 45 may be provided to displace only one of chains 4 or 5 (and the result obtained will be practically the same). The chain however which is subjected only to the alternating vertical movements then has the tendency to stretch out in relation to the other which if prolonged could be prejudicial to the effective operation of the apparatus.

Before describing the operation of the apparatus of this invention, it will be assumed that all the movements of the different devices constituting the apparatus are controlled by a single continuously rotating motor causing one or several cam shafts to rotate. To obtain the step by step movement of the conveyor 1 this continuous rotation motor, for example, an electric motor, is connected to the shaft of 2 or 3 by the well known Maltese Cross or Geneva wheel system which determines correctly the stop or dwell positions of the conveyor 1, whilst are cams actuated during such dwell times to operate, on the one hand, the loader 28, and on the other hand, synchronous peristaltic pumps feeding the distributors 10, 12 and 16. The pump feeding the distributors 19 with rinsing water may likewise be controlled by the cams or it may operate continuously. The electric motors of the fans 23 as well as air heating electric resistances for the heater tunnel 22 operate continuously. The motor of the band 31 may likewise be driven by a Maltese Cross or Geneva wheel system, to achieve step by step motion in synchronism with the band 1 if desired.

It is obvious that the construction of such a driving assembly is within the competence of the expert.

The operation of the apparatus of FIG. 1 will now be described following a slide along its path of motion from loader 28 to receptacle 33. At the initial moment, the apparatus is assumed stopped in the position shown. The loader 28 is actuated which causes the application of the top slide of the stack 29 to the suction cup at location 7. The slide is held by suction by the suction cup and conveyed by step passing in turn through locations 8, until it reaches the location 9. At the moment of its stopping at location 9, the distributor 10 causes the quantity of May Grunwald reagent required to fall onto the slide. The slide then passes to location 11, where it receives a quantity of water which is practically of the same quantity as the May Grunwald reagent previously applied. The water mixes with this reagent. The slide is then subjected, on the one hand, to transverse tilting and rocking movements caused by the plate 45 and to longitudinal tilting movements in passing one of the ramps such as 14 in the course of its passage to the location 15. It is to be noted that between locations 11 and 15, there may be provided several locations each as location 13 instead of a single one. The tilting movements have the effect of displacing or wiping evenly the drop or drops of the mixture on the blood smear, but are such as to avoid the falling of the drops from the slide. In the location 15, the slide receives a predetermined quantity of diluted Giemsa reagent, which spreads naturally and therefore no tilting movements of the slide are required. The colouring and fixing reactions are effected on the slide whilst it passes through location 17. At location 18 the slide is rinsed. It then passes step by step through the locations 20. It may be noted that in the last of these locations 20 the plate 38 of the suction cup supporting the slide is held only by the rod 6 and takes up an inclined position which enhances the flowing off of the excess water in the course of rinsing. The locations 21 as well as possibly certain latter locations 20 are located in the drying tunnel 22 where the slides are dried. Before reaching the location 24, the plate 38 is again returned to horizontal dispostion to present correctly the suction cup 36 to the stop 25. The latter is placed on the path of travel of the suction cup so as to engage a point 47 of the suction cup thereby to deform locally the cup and allow the entry of air into the cup, which releases the slide and it falls onto band 31 wherefrom it is guided towards the container 33. The empty suction cup is then displaced until it again reaches the location 7 completing the cycle.

It is very important to note, for better understanding one of the advantages of the described apparatus, that in the course of the various colouring, fixing, rinsing and drying operations the central region of the underside of the slide 37 located inside the suction cup (this region extends between the points 48 and 49 in FIG. 2) is not contacted by any of the liquids used in the process and therefore remains clean. Now this clean region is in register with smear which facilitates very much, examination under a microscope.

Figure 4:
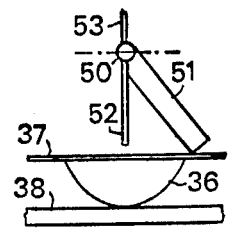
FIG. 4 is a diagrammatic sectional side view of a suction cup carrying a slide, the section being taken on the line V—V of FIG. 3.
Figure 5:
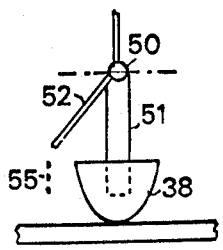
FIG. 5 is a view similar to FIG. 4 but shows the case where the suction cup does not carry a slide.

It may occur in the course of the operation of the apparatus that a suction cup passing from the location 7 does not carry a slide, for example, because the loader is empty, or the slide is not taken up by the cup, the empty suction cup arriving into the location 9 or 15 would receive reagents which would soil its inner surface and it is desirable to avoid this. To this end, as FIGS. 4 and 5 show the outlet pipes of the distributors 10, 12 and 16 are each provided with a hollow shaft capable of turning in fixed bearings (not shown) under the action of an arm 51. The outlet pipe 52 is joined to the connection pipe 53 of the distributor by a hollow shaft 50. Assuming that the suction cup 36 moves from left to right, in FIGS. 4 and 5 when a slide is present as shown in FIG. 4, then slide 37 lifts the arm 51 by its left edge 54 and keeps it raised during the dwell period. The angle between pipe 52 and arm 51 is such as to keep pipe 52 vertical ensuring the pouring of the reagent correctly into the center of the slide. In FIG. 5, the suction cup 36 is shown not carrying any slide. The arm 51 is therefore not raised and at the moment of stopping the pipe 52 remains so inclined to the vertical to cause the drops 55 to fall outside the suction cup 36.

It is obvious that the dimensions of the suction cups are arranged depending upon the size of the slides. These latter preferably overhang the cup rim as shown to obtain a clean action of the device of FIGS. 4 and 5.

It is to be noted that the driving speed of the main motor may be variable according to the preparation of the smears in which other reagents than those mentioned above can be used. For this purpose, the positions of the distributors may likewise be altered. The apparatus, may be used to color vaginal or other smears, as opposed to blood smears.

Although the principles of the present invention have been described in respect of one particular embodiment, it must be understood that the said description has only been made by way of example, and is not intended to limit the general scope of the invention to all the detail herein described.

What I claim is:

1. Apparatus for applying treatment medium to slides, such as slides carrying blood smears, comprising a plurality of suction cups, each cup being approximately the size of the viewing area on said slide, conveying means supporting said cups and adapted to convey the suction cups in an endless path including a horizontal section, means defining a loading station at which smear slides may be attached one by one to the suction cups by being pressed thereto, said suction cup being attached to one side of said slide under the area of the slide which receives said smear, means defining an unloading station at which the slides may be detached from the suction cups, and means defining at least one treatment medium station at which treatment medium can be applied to a smear in said area on the one side of a slide opposite to the side attached to a suction cup when such slide is located on a horizontal section of said endless path and the cup is located under the slide, whereby said suction cup covers and protects said area of said slide while said medium is being applied.

2. Apparatus for applying treatment medium to slides, such as slides carrying blood smears, comprising an endless conveyor means carrying suction cups of elastic material having a size and shape conforming to the viewing area on each of said slides, the backs of the slides adhering to said suction cups during an operation of the apparatus, the point of adherence being in the viewing area opposite the part of the slide which receives a specimen, a loading station for pressing each slide to be treated onto a suction cup and an unloading station for detaching the slides from the suction cups, the path of the said conveyor means having an upper horizontal reach above which are disposed one or more treatment distributors, and a lower horizontal reach, means defining a drying zone at said lower reach, an unloading zone and a loading zone these latter zones being respectively opposite the unloading station and the loading station, and said conveyor means having connecting curve reaches between the said horizontal reaches, the arrangement being that the planes of the slides are practically horizontal when they travel in the horizontal reaches of the conveyor means.

3. Apparatus according to claim 2, including means for moving the endless conveyor means in a step by step movement, and the suction cups being spaced by a pitch equal to a step of such movement.

4. Apparatus according to claim 2 wherein the said loading station comprises a spring loader adapted to contain a batch of slides to be treated, means for application of the slides one by one onto the suction cups, means for pushing the loader towards the suction cups, which are located opposite the slide above the loader, to flatten the suction cups concerned by a predetermined amount, and for releasing the slide from the loader when the predetermined position is reached.

5. Apparatus according to claim 2, wherein said unloading station comprises a travelling band means located below the lower horizontal reach and under the unloading zone, and a fixed stop located in the path of travel of the suction cups so as to deform the latter and thus cause the entry of air in the cavity of the suction cups which releases the slides they carry, so that the slides fall onto the travelling band means and from there to a slide receiving receptacle.

6. Apparatus according to claim 3, wherein there are several distributor means respectively having outlet devices located to be in register with said suction cups when the conveyor dwells between steps, said distributors being adapted to operate at each stopping of the said conveyor in order to pour a predetermined but adjustable quantity of a medium per distributor and means for preventing said pouring of said quantity if a slide is not present on a suction cup.

7. Apparatus according to claim 6, wherein the said outlet devices each have an outlet pipe and a directing device of the said outlet pipe provided with a counterweight, the said counter weight causing the directing device to turn so as to direct the discharge from the outlet pipe outside the suction cup when the latter does not carry any slide and being raised by the slide to direct the said discharge vertically towards the slide when the suction cup carries a slide.

8. Apparatus according to claim 3, including rinsing water distributor means located to be opposite respective suction cups upon the stopping of the conveyor means in dwell positions, said rinsing water distributor being adapted to operate continuously or at a certain adjustable time after each stopping of the conveyor.

9. Apparatus according to claim 2, wherein the said conveyor means comprises two link chains driven by two toothed pinions, the two chains being mounted parallel and coupled by transverse rods which are connected to the links and located in grooves in the underside and towards the leading edge of plates on which the individual suction cups are respectively carried.

10. Apparatus according to claim 9, wherein the conveyor means has associated with the upper reach and partially with the lower reach, horizontal guides which keep the said plates horizontal and provide ramps to cause each plate to tilt, at a perdetermined location around the transverse rod which guides it.

11. Apparatus according to claim 9, including means for slightly raising or lowering at least one chain and for possibly lowering or raising the other chain as the chains travel in said horizontal reach so as to incline, in turn, the slides carried by the suction cups, transversely with regard to their direction of movement.

* * * * *